United States Patent [19]

Frost

[11] Patent Number: 4,923,875

[45] Date of Patent: May 8, 1990

[54] METHOD FOR TREATMENT OF MAST CELL-MEDIATED DERMATOLOGIC DISORDERS

[75] Inventor: Phillip Frost, Miami Beach, Fla.

[73] Assignee: Baker Cummins Pharmaceuticals, Inc., Miami, Fla.

[21] Appl. No.: 377,572

[22] Filed: Jul. 10, 1989

[51] Int. Cl.$^5$ ............................................. A61K 31/44
[52] U.S. Cl. ................................................... 514/282
[58] Field of Search ........................................ 514/282

[56] References Cited

U.S. PATENT DOCUMENTS 4,416,886 11/1983 Bernstein ............................ 424/260

OTHER PUBLICATIONS

Chem. Abstracts, vol. 104 (1986), 213272t.
Summerfield, *Br. J. Clin. Pharmac.*, 10:180–183 (1980).
Bernstein et al., *J. Am. Acad. Derm.*, 5:227–228 (1981).
Gal et al., *Anesthesiology*, 63:A508 (1985).

Ho et al., *Gastroenterology*, 88:1665 (1985) (Orbit Database Abstract).
Dixon et al., *J. Pharm. Sci.*, 73:1645–1646 (1984).
Dixon et al., *Clin. Pharmacol. Ther.*, 39:49–53 (1986).
Thornton and Losowsky, *Brit. Soc. Gastroenterology*, Abstract from Spring Meeting (3/23–3/25/88).
Thornton and Losowsky, *Br. Med. J.*, 297:1500–1504 (1988).

*Primary Examiner*—Stanley J. Friedman
*Attorney, Agent, or Firm*—Kirschstein, Ottinger, Israel & Schiffmiller

[57] ABSTRACT

A method of treating human or animal patients suffering from mast cell-mediated dermatological disorders comprising the administration to the affected skin areas of a topical composition comprising from about 0.01 to about 10% by weight of the narcotic antagonist nalmefene or one of its salts or esters in a pharmaceutically inert topical vehicle. Compositions suitable for use in such methods include solutions, aerosols, creams, gels, ointments and lotions. The compositions may be applied to the affected areas from 1 to about 6 times daily.

10 Claims, No Drawings

METHOD FOR TREATMENT OF MAST CELL-MEDIATED DERMATOLOGIC DISORDERS

BACKGROUND OF THE INVENTION

1. Field of the Invention

The invention relates to methods and compositions for the treatment for acute dermatitis.

2. Description of the Prior Art

There are different forms of dermatitis (inflammation of skin); erythema, edema, papular eruptions and pruritus may be present in both human and animal dermatitides.

It is known that the symptoms present in some forms of dermatitis are caused by degranulation of cutaneous mast cells, resulting in, inter alia, histamine release. Oral and topical antihistamines are thus used to treat the manifestations of mast-cell mediated dermatoses.

Many dermatitic conditions also respond to topical corticosteroids of low to medium potency, and such agents are often used in treating the inflammatory and pruritic manifestations of acute dermatitis. Topical antipruritic agents (e.g., menthol, phenol and camphor) and anesthetics (most commonly, benzocaine) are also frequently applied to treat moderately extensive dermatitic eruptions.

All of the foregoing pharmaceutical agents conventionally used to treat mast cell-mediated dermatologic disorders suffer from significant drawbacks. Topical corticosteroids can cause epidermal and dermal atrophy, resulting in thinning of the skin and striae, particularly in highly absorptive areas. If applied to extensive areas or with prolonged use of occlusive dressings, corticosteroids may be absorbed in sufficient quantities to cause the same adverse systemic effects observed with orally or parenterally administered steroids, including pernicious effects on the endocrine and immune systems. Topical antihistamines and anesthetics are not very effective, may be sensitizing and, in some instances, actually cause allergic contact dermatitis. Oral antihistamines are often associated with sedative side effects. Antipruritic agents such as camphor and menthol usually provide only short-term symptomatic relief for pruritus.

SUMMARY OF THE INVENTION

It is the object of the present invention to provide compositions and methods for the treatment of mast cell-mediated dermatologic disorders which avoid the aforementioned drawbacks of the prior art treatment agents and methods while providing effective relief. In keeping with this object and others that will become apparent hereinafter, the present invention resides in the treatment of such disorders through the topical application of pharmaceutical compositions containing as their active ingredient from about 0.01 to about 10% by weight of the narcotic antagonist nalmefene.

DETAILED DESCRIPTION OF THE INVENTION

Nalmefene (6-methylene-6-desoxy-N-cyclopropylmethyl-14-hydroxydihydronormorphine) is a long-acting, orally available, potent narcotic antagonist with pure antagonist activity. Apart from its utility in antagonizing the sedation, respiratory depression and other actions of opioid agents, nalmefene has also been found useful in treating diverse conditions such as hyperkinesia in children (U.S. Pat. No. 4,454,142), senile dementia (U.S. Pat. No. 4,511,570) and sudden infant death syndrome (U.S. Pat. No. 4,639,455), among others. Nalmefene has not hitherto been disclosed, however, as having any utility in the treatment of acute dermatitis or any related skin conditions, nor have topical formulations of nalmefene been utilized for any purpose.

The method of the present invention consists of the topical application to an affected skin area of a human or animal patient suffering from a mast cell-mediated dermatologic disorder of a topical pharmaceutical composition comprising from about 0.01 to about 10% nalmefene by weight in a pharmaceutically acceptable inert carrier. A preferred concentration range is from about 0.1 to about 2.5% nalmefene by weight. Suitable carriers or vehicles for such compositions include, without limitation, conventional ointments, creams, gels, aerosols, lotions and liquid solutions known to those skilled in the medicinal and pharmaceutical arts. Many examples of such suitable topical vehicles are set forth in *Remington's Pharmaceutical Sciences,* 17th edition (1985) and variations of these vehicles which include penetration enhancers.

The active ingredient used in the methods and compositions of the present invention may be nalmefene base, or pharmaceutically acceptable salts or esters of nalmefene, e.g., nalmefene hydrochloride or nalmefene glucuronide.

Preferred inert vehicles or carriers for use in the present invention are those which are chemically compatible with nalmefene or its salts or esters, form stable solutions, emulsions, dispersions or suspensions of the active ingredient and promote rapid release and absorption of the drug upon application to the affected skin areas.

In accordance with the novel methods, a quantity of a lotion, cream, gel or ointment containing nalmefene (or one of its salts or esters) sufficient to form a thin film or coating over the affected skin area is applied from 1 to about 6 times daily for as long as the symptoms persist. Examples of conditions which may be effectively treated with the subject methods and compositions include, but are not limited to, urticaria, contact dermatitis, atopic dermatitis, allergic dermatitis, reactions to intradermal allergy testing, mast cell disease, eczematous dermatitis and dermatitis caused by insect bites or stings. Rapid relief of itching and erythema is achieved.

In the case of liquid solutions or aerosol sprays containing nalmefene base, salts or esters, a sufficient quantity of the liquid to throughly wet the affected area should be applied. This treatment may be repeated from 1 to about 6 times daily as needed.

The following Examples provide detailed illustrations of the compositions and methods of the present invention. The Examples are not intended, however, to limit or restrict the scope of the invention in any way, and should not be construed as providing formulations or methods of administration which must be utilized exclusively to practice the present invention.

EXAMPLE 1

Liquid Solution

Nalmefene (1 g) is dissolved in 49 g dimethylisosorbide to yield a 2% nalmefene solution by weight. That solution is then diluted with 50 g ethyl alcohol to yield a 1% solution of nalmefene.

EXAMPLE 2

Creams

(a) Oil in Water

Nalmefene (0.5 g) is dissolved in a mixture of diisopropyl adipate (7 g), polyoxyl-50 stearate (1 g) and glyceryl stearate (5 g) at 70° C. with stirring. After dissolution, the mixture is diluted with sufficient purified water to reach a total weight of 100 g and allowed to cool with stirring.

(b) Water in Oil

Nalmefene (0.5 g) is dissolved in a mixture of stearic acid (10 g), squalene (10 g), isopropyl myristate (10 g) and mineral oil (5 g) at 70°–80° C. with stirring. After dissolution, the following ingredients are added successively to the above:

| | |
|---|---|
| Petrolatum | 2.0 g |
| Cetyl alcohol | 1.0 g |
| Sobitan monostearate | 4.0 g |
| Tween 60 (ICI Americas, Inc.) | 4.0 g |
| Propyl paraben | 0.2 g |
| BHT | 0.05 g |
| Glycerin | 1.0 g |
| Triethylamine | 0.5 g |
| Methyl paraben | 0.1 g |
| Purified water | 51.65 g |

The formulation is allowed to cool with stirring.

Alternatively, up to 25 g isopropyl myristate may be used in the above formulation.

EXAMPLE 3

Ointment

Nalmefene (300 mg) is dissolved in 900 mg cetyl alcohol. An ointment is then compounded with 900 mg white wax (melted) and 27.9 g petrolatum.

EXAMPLE 4

Gel

Nalmefene (0.5 g) is mixed with 3 g dimethylisosorbide. The resultant mixture is added to 88.5 g SDA 40 alcohol with stirring. Propylene glycol (5 g) is added, followed by slow addition of 3 g hydroxypropyl cellulose. Stirring at a slow rate is continued for 2.5 hrs, during which time a gel forms.

EXAMPLE 5

Lotion

Nalmefene (1 g) is admixed with the following ingredients to form a homogeneous lotion:

| | |
|---|---|
| Mineral oil | 21.0 g |
| Isopropyl palmitate | 1.5 g |
| Glyceryl stearate | 3.0 g |
| Cetyl alcohol | 1.5 g |
| Tween 60 | 2.5 g |
| Polyoxyl 40-stearate | 0.5 g |
| Propylene glycol | 2.0 g |
| Purified water | 67.0 g |

EXAMPLE 6

Aerosol

Nalmefene (1 g) is dissolved in 90 g ethyl alcohol. Acetylated lanolin alcohol, povidone, tris (hydroxymethyl)-amino methane, wheat germ glycerides and sufficient purified water are added for a total weight of 100 g.

EXAMPLE 7

In a double-blind study, 30 subjects were treated with the gel of Example 4 (or a similar gel containing 1% nalmefene) and placebo for pruritus and irritation incident to intradermal skin testing for allergies. All patients reported greater relief with nalmefene gel than with placebo.

EXAMPLE 8

In an open study, six subjects suffering from common insect bites reported relief from inflammation and pruritus after application of the gel of Example 4 and/or the liquid solution of Example 1.

It has thus been shown that there are provided methods and compositions which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims:

1. A method of treating an affected skin area of a human or animal patient suffering from a mast cell-mediated dermatologic disorder comprising the topical application to the skin area of said patient of an effective amount of a pharmaceutical composition comprising (a) from about 0.01 to about 10% by weight of a compound selected from the group consisting of nalmefene and its pharmaceutically acceptable salts and esters, and (b) an inert pharmaceutical carrier.

2. A method according to claim 1 wherein said pharmaceutical composition comprises from about 0.1 to about 2.5% by weight of said compound.

3. A method according to claim 1 wherein said compound is nalmefene.

4. A method according to claim 3 wherein said composition comprises 1% nalmefene by weight.

5. A method according to claim 3 wherein said composition comprises 0.5% nalmefene by weight.

6. A method according to claim 1 wherein said compound is nalmefene hydrochloride.

7. A method according to claim 1 wherein said compound is nalmefene glucuronide.

8. A method according to claim 1 wherein said inert carrier is selected from the group consisting of liquid solutions, aerosols, lotions, creams, gels and ointments.

9. A method according to claim 1 wherein said disorder is selected from the group consisting of urticaria, contact dermatitis, atopic dermatis, allergic dermatitis, reactions to intradermal allergy testing, mast cell disease, eczematous dermatitis and dermatitis caused by insect bites or stings.

10. A method according to claim 1 wherein said composition is applied from 1 to about 6 times daily.

* * * * *